(12) United States Patent
Umeno

(10) Patent No.: US 7,503,939 B2
(45) Date of Patent: *Mar. 17, 2009

(54) HAIR COLOR

(75) Inventor: Takashi Umeno, Fujioka (JP)

(73) Assignee: Mitsubishi Pencil Co., Ltd., Tokyo (JP)

( * ) Notice: Subject to any disclaimer, the term of this patent is extended or adjusted under 35 U.S.C. 154(b) by 247 days.

This patent is subject to a terminal disclaimer.

(21) Appl. No.: 10/588,299

(22) PCT Filed: Feb. 2, 2005

(86) PCT No.: PCT/JP2005/001501

§ 371 (c)(1),
(2), (4) Date: Aug. 2, 2006

(87) PCT Pub. No.: WO2005/074874

PCT Pub. Date: Aug. 18, 2005

(65) Prior Publication Data

US 2007/0130701 A1    Jun. 14, 2007

(30) Foreign Application Priority Data

Feb. 3, 2004  (JP) .............................. 2004-026621

(51) Int. Cl.
*A61Q 5/10* (2006.01)
(52) U.S. Cl. ...................... 8/405; 8/406; 8/435; 8/552; 8/581; 8/632
(58) Field of Classification Search .................... 8/405, 8/406, 435, 552, 581, 632
See application file for complete search history.

(56) References Cited

U.S. PATENT DOCUMENTS

| 5,948,124 A | 9/1999 | Grit | |
|---|---|---|---|
| 2002/0046431 A1* | 4/2002 | Laurent et al. | 8/405 |
| 2003/0019053 A9 | 1/2003 | Rondeau | |
| 2003/0066142 A1* | 4/2003 | Tsuchiya | 8/405 |
| 2004/0148711 A1 | 8/2004 | Rondeau | |

FOREIGN PATENT DOCUMENTS

| JP | 10-72327 A | 3/1998 |
|---|---|---|
| JP | 11-343218 A | 12/1999 |
| JP | 2001-172141 A | 6/2001 |
| JP | 2003-246714 A | 9/2003 |

* cited by examiner

*Primary Examiner*—Eisa B Elhilo
(74) *Attorney, Agent, or Firm*—Buchanan Ingersoll & Rooney PC

(57) ABSTRACT

A hair color which includes 0.5 to 8% by weight of a basic dye as a coloring agent, 0.5 to 15% by weight of a alcohol-soluble resin, 20 to 80% by weight of lower alcohol and 5 to 50% by weight of water. The hair color does not require washing of the hair immediately after being applied and enables the hair to be gradually dyed upon repeated use. The hair color can provide excellent water resistance against sweat and rain in a hot and humid period such as a summer season.

12 Claims, 5 Drawing Sheets

HAIR COLOR

TECHNICAL FIELD

The present invention relates to a cumulatively dying hair color which does not require washing of hair immediately after used and by which the hair is gradually dyed with repeating of use.

BACKGROUND ART

Permanent hair colors (oxidative hair colors) and semi-permanent hair colors (acid hair colors) which have so far generally been used have such large defects that dying operation in use is complicated and troublesome and that the circumference, cloths and the skin of persons applied are dyed.

Accordingly, they have to be applied usually in beauty salons or they have to be applied by ourselves at the time of bathing so that they can be washed away soon even if stained, and therefore an excessive burden has been forced to the users.

A cumulatively dying temporary hair color (refer to patent document 1) provided by the present applicants which comprises 0.01 to 3% by weight of an acid dye as a coloring agent, 1.5 to 10% by weight of a nonionic or anionic silicone base resin, 3 to 20% by weight of a hair dying auxiliary, 30 to 80% by weight of a lower alcohol and 5 to 50% by weight of water and which has a pH of 2 to 5 and a viscosity of 100 mPa·s or less is known as a hair color which can reduce the above burdens and which can cumulatively dye hair by easily repeating use even if dying per once is little.

Further, a hair cosmetic (refer to patent document 2) which comprises a basic dye and an amphoteric polymer resin and which has a pH of 3.0 to 8.0 is known as a cosmetic which does not dye the skin and has the effect that it colors gradually the hair.

The hair color disclosed in the patent document 1 described above is excellent as a hair color which can cumulatively dye hair, but since an acid dye is used, a little problem is involved therein in that the skin is dyed in a case where the liquid adheres onto the skin of scalp and the fingertip to force a burden to the users. In addition thereto, the above hair color comprises an acidic liquid, and therefore involved therein is the problem that the dispersibility of a pigment is inferior when it is blended.

The hair cosmetics disclosed in the patent document 2 described above are common in that a basic dye is used, but a problem is involved therein in that water resistance and the cumulative dying property are inferior and in that the liquid tends to be increased in a viscosity, so that the coating property is deteriorated.

Patent document 1: Japanese Patent Application Laid-Open No. 172141/2001 (claims, examples and others)

Patent document 2: Japanese Patent Application Laid-Open No. 246714/2003 (claims, examples and others)

DISCLOSURE OF THE INVENTION

Problems to be Solved by the Invention

In light of the problems on the conventional arts described above, the present invention intends to solve them, and an object thereof is to provide a hair color which does not dye the skin and is excellent in a cumulative dying property and which has excellent water resistance against sweat and rain in a hot and humid period such as a summer season.

Means for Solving the Problems

Intensive studies repeated by the present inventors on the problems of the conventional arts described above have resulted in finding that a hair color meeting the object described above can be obtained by controlling contents of a basic dye, a specific alcohol-soluble resin and a lower alcohol respectively to specific ranges, and thus the present invention has come to be completed.

That is, the present invention comprises the following items (1) to (5).

(1) A hair color comprising 0.5 to 8% by weight of a basic dye as a coloring agent, 0.5 to 15% by weight of an alcohol-soluble acryl base resin, 20 to 80% by weight of a lower alcohol and 5 to 50% by weight of water.

(2) The hair color as described in the above item (1), wherein the alcohol-soluble acryl base resin is a silicone·acryl block copolymer.

(3) The hair color as described in the above item (1) or (2), further comprising carbon black.

(4) The hair color as described in the above item (3), wherein a content of the carbon black is 0.1 to 3% by weight based on the total amount of the hair color.

(5) The hair color as described in anyone of the above items (1) to (4), wherein the hair color has a viscosity of 20 mPa·s or less.

EFFECTS OF THE INVENTION

According to the present invention, provided is a hair color which is excellent in a cumulative dying property and usability and which has excellent water resistance against sweat and rain in a hot and humid period such as a summer season.

BRIEF DESCRIPTIONS OF THE DRAWINGS

EXPLANATIONS OF THE REFERENCE LETTERS AND NUMERALS

Figure 1:
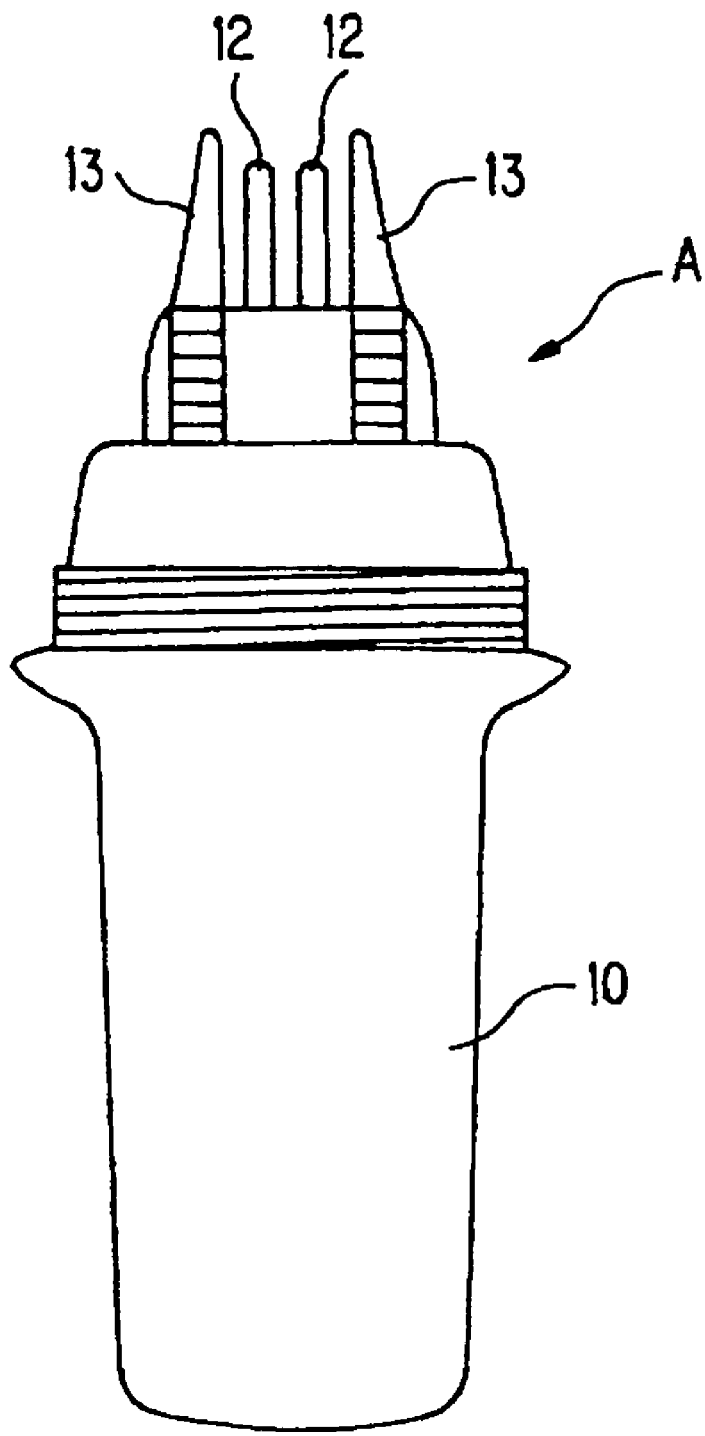
FIG. 1 is a side view showing one example of the embodiment of the present invention.

A: Applicator for hair
10: Applicator main body
12: Feed (pen feed)
13: Comb part

BEST MODE FOR CARRYING OUT THE INVENTION

The embodiment of the present invention shall be explained below in detail.

The hair color of the present invention is characterized by comprising 0.5 to 8% by weight of a basic dye as a coloring agent, 0.5 to 15%by weight of an alcohol-soluble acryl base resin, 20 to 80% by weight of a lower alcohol and 5 to 50% by weight of water.

The basic dye used in the present invention shall not specifically be restricted as long as it is permitted to be used for a hair color and is water-soluble, and it includes, for example, BASIC RED 1, BASIC RED 2, BASIC RED 22, BASIC RED 46, BASIC RED 76, BASIC RED 118, BASIC YELLOW 11, BASIC YELLOW 28, BASIC YELLOW 57, BASIC BLUE 3, BASIC BLUE 6, BASIC BLUE 7, BASIC BLUE 9, BASIC BLUE 26, BASIC BLUE 41, BASIC BLUE 99, BASIC GREEN 1, BASIC GREEN 4, BASIC BROWN 4, BASIC BROWN 16, BASIC BROWN 17, BASIC ORANGE 1, BASIC ORANGE 2, BASIC VIOLET 1, BASIC VIOLET 3, BASIC VIOLET 4, BASIC VIOLET 10, BASIC VIOLET 11, BASIC VIOLET 14 and BASIC VIOLET 16, and they can be used alone or in a mixture of two or more kinds thereof.

A content of the above basic dyes has to be 0.5 to 8% by weight (hereinafter referred to merely as [%]) based on the total amount of the hair color, and it is preferably 0.8 to 5%.

If the above content of the basic dye is less than 0.5%, the hair dying effect is not sufficiently exerted. On the other hand, if it exceeds 8%, stain to the others such as the skin is liable to be brought about. Accordingly, both ranges are not preferred.

The alcohol-soluble acryl base resin used in the present invention enhances the sweat resistance and the water resistance in using for the hair of the whole head without damaging the temporary coloring property and the accumulative dying property and further inhibits stain caused by secondary adhesion onto the skin and the cloths which is liable to be caused in a hot and humid period such as a summer season. In addition thereto, when adding carbon black described later, it can enhance dispersibility of the carbon black and can provide the hair with suitable setting ability.

The alcohol-soluble acryl base resin used in the present invention includes silicone·acryl block copolymers which are synthesized from silicone such as polydimethylsiloxane and acryl base polymers of methacrylic acid and alkyl methacrylate using a high molecular azo polymerization initiator and which are soluble in alcohols such as ethanol.

The above silicone·acryl block copolymer is provided with the properties of both the resins in combination and can provide the hair color with smooth feeling (water repellant property and lubricity) of a silicone base polymer and film-forming ability of an acryl base polymer to a maximum extent.

The alcohol-soluble acryl base resin used in the present invention is used preferably in a solution form in which the silicon·acryl block copolymer described above is dissolved in ethanol, denatured alcohol or a mixed solution thereof from the viewpoint of usability, handling and the like.

The alcohol-soluble acryl base resin which can specifically be used includes alkyl acrylate/dimethicone copolymers [another name: methacrylic acid·alkyl methacrylate·dimethylpolysiloxane block copolymer, MAIBLOCKWAKO 101 (ethanol solution having a solid content of 25%, manufactured by Wako Pure Chemical Industries, Ltd.) available as a commercial product], octylacrylamide/acryl resins and AMPHOMER V-42 and DERMACRYL-79 (all manufactured by Nippon NSC Co., Ltd.) available as a commercial product.

A content of the alcohol-soluble acryl base resin described above in the present invention has to be 0.5 to 15% in terms of solid based on the total amount of the hair color, and it is preferably 1 to 10%, more preferably 1.5 to 5%.

If the above content of the alcohol-soluble acryl base resin is less than 0.5%, the sweat resistance and the water resistance are poor. On the other hand, if it exceeds 15%, the viscosity is too high, and the coating property is deteriorated. In addition thereto, the cumulative dying property is deteriorated. Accordingly, both ranges are not preferred.

For example, at least one of lower alcohols which can be used for a hair color, such as ethyl alcohol (ethanol), propanol, butanol, isopropanol and isobutanol is used as the lower alcohol used in the present invention, and ethyl alcohol is preferred in terms of the stability, the drying property and the odor.

A content of the lower alcohol described above has to be 20 to 80% based on the total amount of the hair color, and it is preferably 40 to 70%.

If the above content of the lower alcohol is less than 20%, the drying property is lowered. On the other hand, if it exceeds 80%, the hair dying effect is not sufficiently exerted. Accordingly, both ranges are not preferred.

The balance of the hair color in the present invention is controlled by water, and refined water, ion-exchanged water, purified water, extra-purified water, clean water, distilled water and deep ocean water can be used. A content thereof has to be 5 to 50% based on the total amount of the hair color, and it is more preferably 15 to 40%.

If the above content of water is less than 5%, the hair dying effect is reduced. On the other hand, if it exceeds 50%, the drying property is reduced. Accordingly, both ranges are not preferred.

The hair color of the present invention can exhibit the color tones of hair having the respective colors by the basic dyes described above, and if it is a hair color for gray hair which further masks gray hair, carbon black is preferably further added.

In the present invention, the silicone acryl block copolymer which is excellent in dispersibility of pigments and the like is used, and therefore dispersibility of carbon black is excellent as well.

The carbon black which can be used includes commercially available carbon blacks produced by the respective production processes, such as furnace black, channel black, acetylene black and the like, to be specific, Special Black 6, Color Black S170 and SB-4 (all manufactured by Degussa Co., Ltd.) and the like, but it shall not specifically be restricted to them.

A content of the above carbon black is preferably 0.1 to 3%, more preferably 0.5 to 1.5% based on the total amount of the hair color.

If the above content of the carbon black is less than 0.1%, the hair color is inferior in terms of sufficiently masking the gray hair. On the other hand, if it exceeds 3%, the viscosity goes up rapidly, and that is not preferred from the viewpoint of the usability.

Further, the hair color of the present invention contains preferably a hair dying auxiliary agent from the viewpoint of exerting a further hair dying effect.

For example, one or a mixture of two or more kinds selected from compounds which are used in conventional semi-permanent hair colors such as benzyl alcohol, phenylethyl alcohol, phenoxyethanol, propylene glycol, N-methylpyrrolidone, gluconic lactone, levulinic acid, urea, ethylene carbonate, N-methyl-2-pyrrolidone, α-ketoglutaric acid, γ-butyrolactone, propionamide and acetamide can be used as the hair dying auxiliary agent.

A content of the above hair dying auxiliary agents is preferably 2 to 20%, more preferably 5 to 15% based on the total amount of the hair color.

If the above content of the hair dying auxiliary agents is less than 2%, the hair dying effect is not sufficiently exertes. On the other hand, if it exceeds 20%, the drying property after coating is reduced, and therefore both ranges are not preferred.

The hair color of the present invention can suitably contain other optional components as long as the effects of the present invention and the stability of the system are not damaged, and it can contain, for example, various surfactants, antiseptic agents, antioxidants, reduction preventives, chelating agents, UV absorbers, viscosity-controlling agents, oil components, silicone derivatives, pigments, perfumes, animal and vegetable extracts and publicly known polymer components.

The hair color of the present invention is controlled preferably to a pH of 5 to 9, more preferably 6 to 8 from the view points of using basic dyes, preventing hair damage and preventing skin stimulation.

If the above pH of the hair color is less than 5, the cumulative dying effect is reduced. On the other hand, if it exceeds 9, damage of the hair and skin stimulation are liable to be brought about by alkali. Accordingly, both ranges are not preferred.

In the present invention, the pH can be controlled by using optionally ordinary pH controlling agents, for example, organic and inorganic bases such as triethanolamine, potassium hydroxide and sodium hydroxide and organic and inorganic acids such as citric acid, malic acid, hydrochloric acid and glycolic acid.

A viscosity of the hair color of the present invention is controlled to 20 mPa·s or less, preferably 10 mPa·s or less and more preferably 2 to 6 mPa·s from the viewpoint of easiness in applying on the hair.

If the above viscosity of the hair color exceeds 20 mPa·s, it is difficult to apply and spread it thinly and evenly on the hair, and therefore that is not preferred.

The hair color in the present invention can be produced by blending the respective components of the basic dye, the alcohol-soluble acryl base resin, the lower alcohol and water each described above in the ranges of the contents described above and homogeneously stirring and mixing them.

The hair color of the present invention thus constituted can suitably be used as a hair coloring material for black hair and a hair coloring material for gray hair, and is the hair color which does not dye the skin and is excellent in a cumulative dying property and which has excellent water resistance against sweat and rain in a hot and humid period such as a summer season.

In using the hair color of the present invention thus constituted, an applicator for hair is used, and the shape and the structure of the applicator for hair shall not specifically be restricted.

In the present invention, the applicator for hair which can be used includes preferably, from the viewpoints of the applying property on the hair, controlling of a liquid amount contained in the applying part, less stain caused on cloths, skin and furniture and the usability, an applicator for hair which is equipped with an applicator main body having a storing part for storing the hair color of the present invention in an inside and an applying part provided at a tip part of the applicator main body and which allows the hair color of the present invention to discharge from the hair color storing part to the applying part to apply the hair color on the hair.

Figure 2:
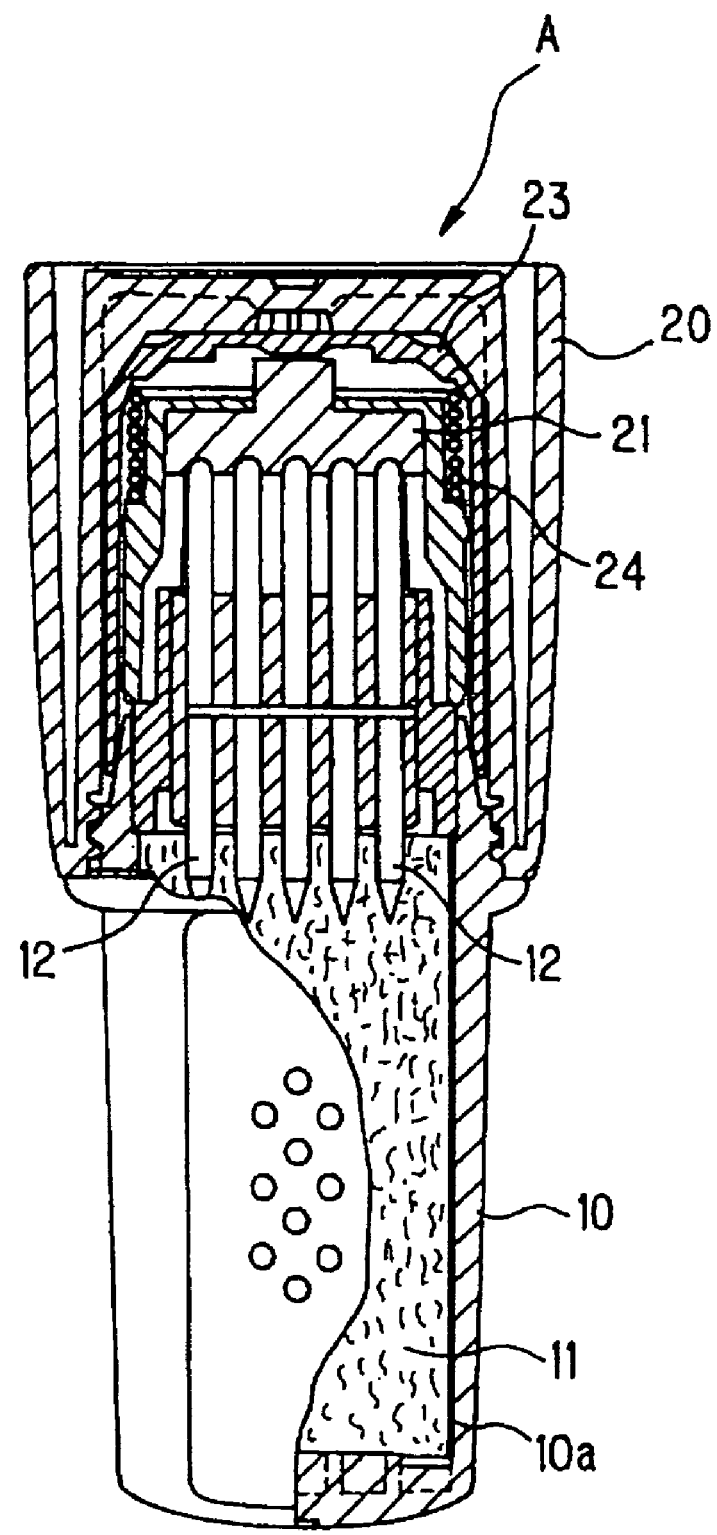
FIG. 2 is a vertical cross-sectional drawing of a side view mode in FIG. 1.
Figure 3:
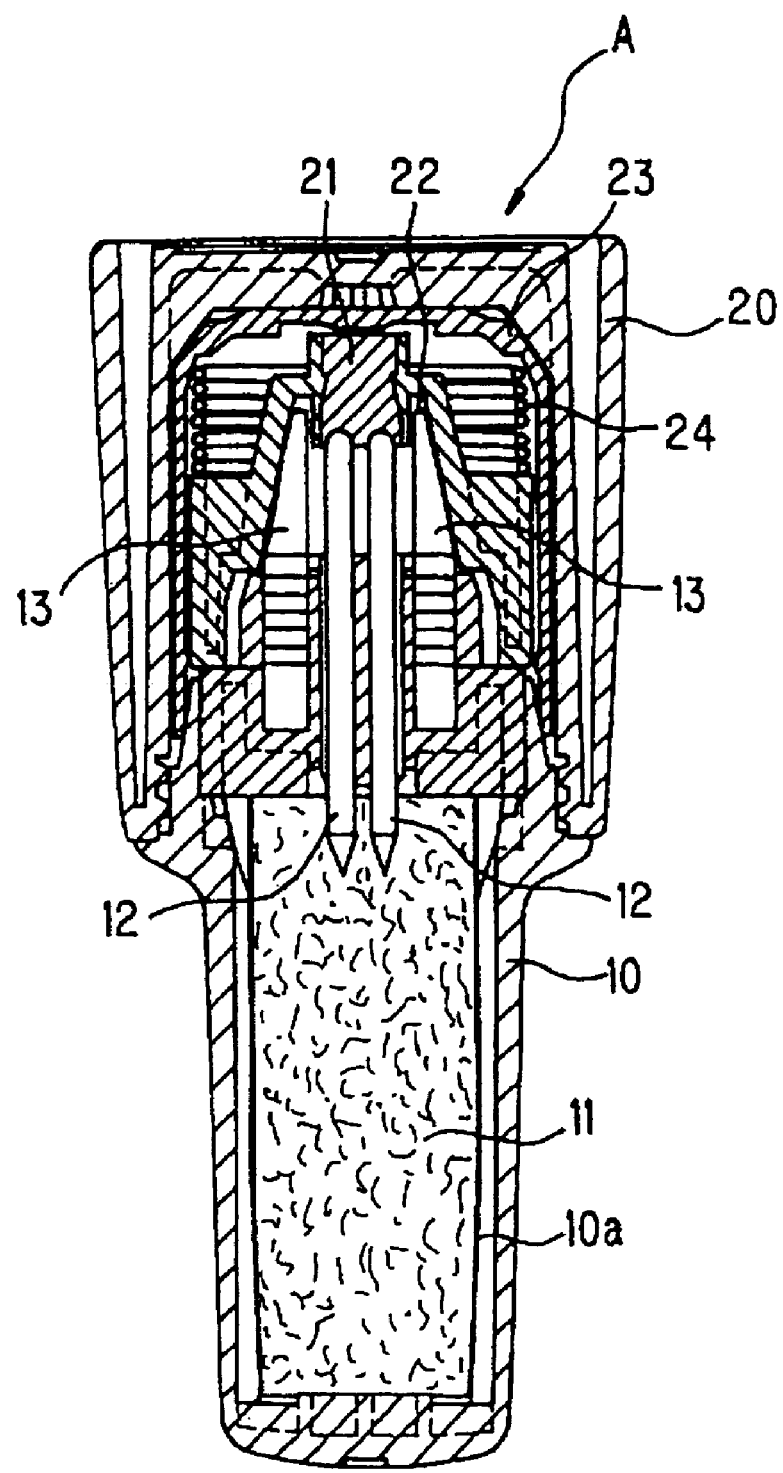
FIG. 3 is a vertical cross-sectional drawing of a front view mode in FIG. 1.
Figure 4:
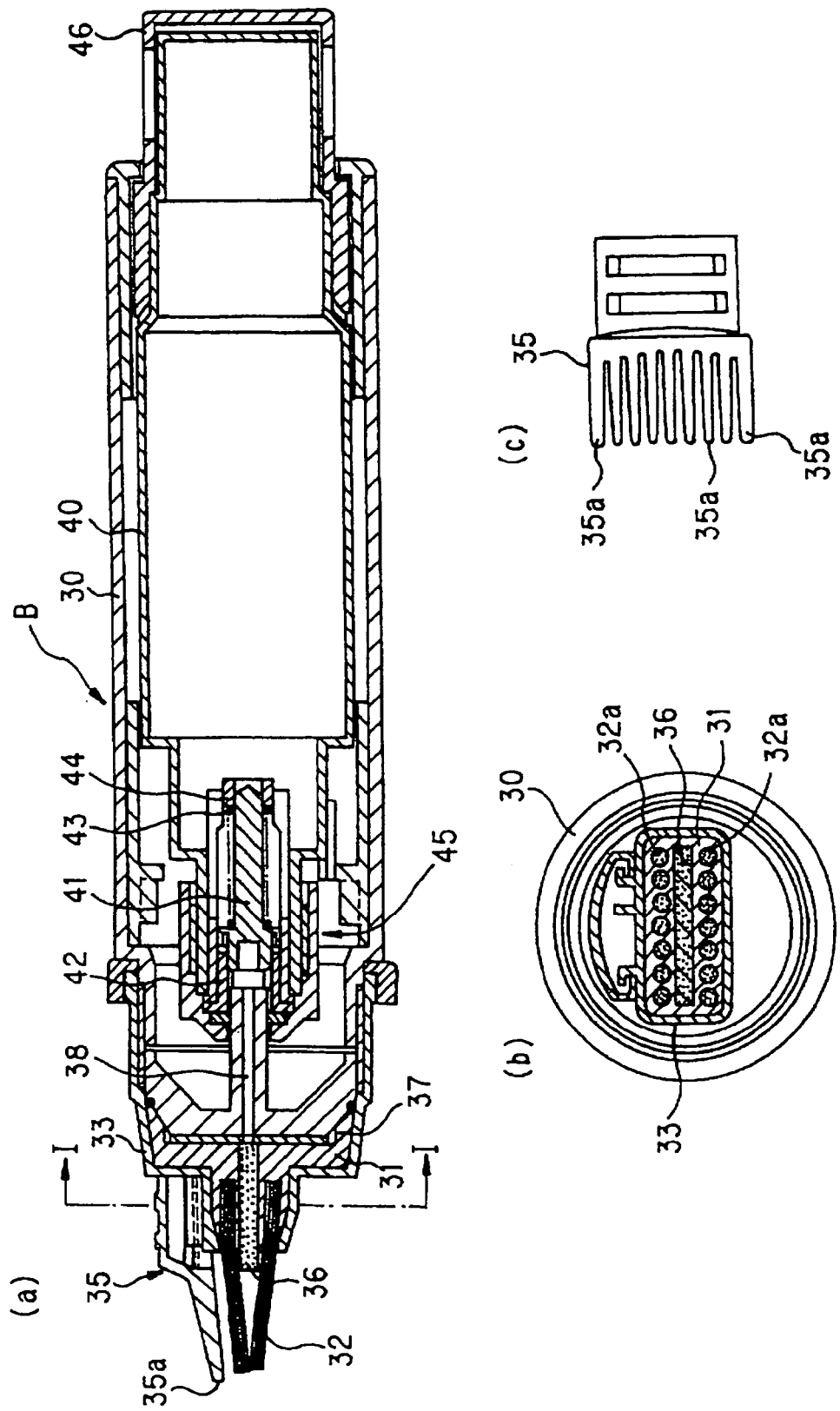
FIG. 4(*a*) is a vertical cross-sectional drawing showing another example of the embodiment of the present invention; (*b*) is an I-I line cross-sectional drawing; and (*c*) is a plain drawing of a comb body.
Figure 5:
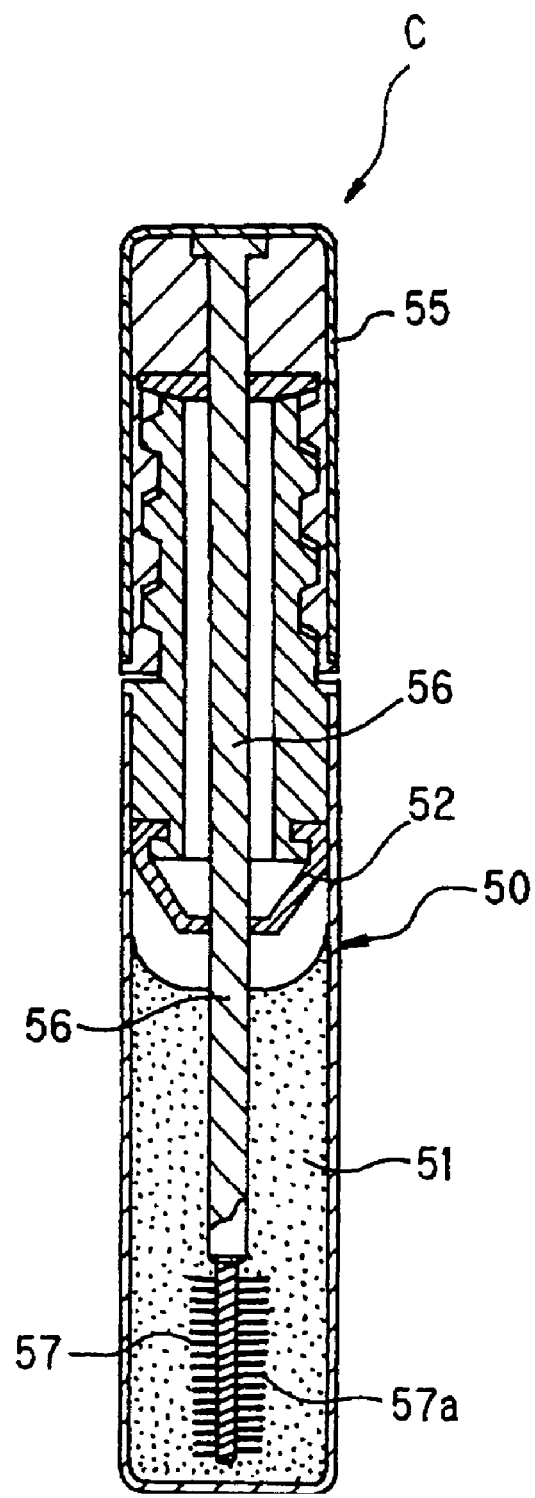
FIG. 5 is a vertical cross-sectional drawing showing another example of the embodiment of the present invention.

The applicator for hair comprising the above structure includes, for example, an applicator A for hair shown in FIG. 1 to FIG. 3, an applicator B for hair shown in FIG. 4 and an applicator C for hair shown in FIG. 5. These applicators A to C for hair shall specifically be explained below.

The applicator A for hair is an applicator of a so-called sliver type (occlusion body), wherein an occlusion body 11 absorbing a hair color having the constitution described above is, as shown in FIG. 1 to FIG. 3, mounted in a hair color storing part 10a in the inside of a barrel 10 constituting an applicator main body; feeds (pen feeds) 12 which are plural combs having capillary action for application are fixed at a tip part of the barrel 10 in an arrangement of linear lines; the rear parts of the feeds 12 are connected with the occlusion body 11, and the tip parts of the feeds 12 are projected to a front of the barrel 10; comb parts 13 are linearly disposed at a side part of the feeds 12; a cap main body 20 is provided at a tip part of the barrel 10 detachably by screwing; it is possible to mount a feed tip-receiving member 21 of a felt with which the tip parts of the feeds 12 are brought into contact; an inner cap 23 in which a concave part 22 for receiving the tip parts of the comb parts 13 is provided in a side part of the feed tip-receiving member is disposed in the inside of the cap main body 20 movably in an axis direction and rotatably in a circumferential direction; and it is possible to allow the inner cap 23 to be forced in an aperture direction of the cap main body 20 by a spring member 24.

In the applicator A for hair comprising the above constitution, the necessary hair color is fed from the occlusion body 11 absorbing the hair color of the present invention having the constitution described above in the storing part 10a to the tip parts of the feeds 12 which are the applying parts, however "blobbing" and unexpected discharge of the liquid are not caused. It can be an applicator for hair which is excellent in carrying and handling properties as well as usability, water resistance and a cumulative hair dying property.

When using the hair color of the present invention by means of the above applicator A for hair, the scalp can be avoided to the utmost from being stained since it has the feeds 12 as a tip applicator, and the hair color can readily be applied onto the hair close to the scalp (the borders of the hair). Accordingly, in the applicator A for hair, the hair color can temporarily be held in the occlusion body making the best use of the properties of the hair color according to the present invention, and an optimum amount of the hair color can be applied onto the hair via the applying part.

The applicator B for hair is an applicator equipped with a valve device of a knocking type, wherein a pedestal 31 is, as shown in FIG. 4(a) to (c), firmly fixed to a tip part of an applicator main body 30, and an applying part 32 comprising brush members 32a, 32a - - - is mounted in the pedestal 31; a tip barrel 33 is firmly fixed to a circumference of the pedestal 31, and a comb member 35 equipped with comb teeth 35a, 35a - - - is detachably mounted on the tip barrel 33; an impregnating member 36 brought into contact with the applying part 32 and comprising sponge and the like is interfitted into a central hole of the pedestal 31, and a hair color guiding tube 38 communicating with a tip of a valve device described later is mounted at the rear of the pedestal 31 so that a stopper 37 for the impregnating member is interposed therebetween.

A cylindrical inner barrel 40 which is a hair color storing part is provided in the inside of the applicator main body 30; a valve device 45 comprising a valve rod 41, a valve seat 42, a valve spring 43 and a spring receiver 44 is mounted on a tip part the inner barrel, and a knocking member 46 is provided at the rear end thereof.

In the applicator B for hair comprising the above constitution, the storing part 40 described above is filled with the hair color having the constitution described above, and the knocking member 46 is knocked, whereby the hair color is discharged to the impregnating member 36 via the hair color guiding tube 38, and it is supplied to the applying part 32 comprising the brush members 32a, 32a - - - and used.

The above applicator B for hair assumes a structure in which the hair color is supplied from the impregnating member 36 to the applying part 32 comprising the brush members 32a, 32a ---, so that it does not cause "blobbing" and unexpected discharge of the liquid, and the hair color is not adhered onto the fingers and the like since it is provided with the comb part 35. Further, it can be an applicator for hair which is excellent in carrying and handling properties as well as usability, water resistance and a cumulative hair dying property.

Further, the applicator C for hair is an applicator of a mascara type, and it is, as shown in FIG. 5, equipped with an applicator main body 50 which is a bottomed cylindrical body and a cap member 55 which hermetically seals an upper end aperture part of the applicator main body 50 by screwing.

The applicator main body 50 is provided in the inside with a storing part 51 for a hair color, and a wiping part 52 is mounted in an upper part of the storing part 51. An applying rod 56 is firmly fixed to the cap member 55, and an applying part 57 comprising brush members 57a, 57a --- is mounted at a tip of the applying rod 56.

In the applicator C for hair comprising the above constitution, when screwing of the cap member 55 is released to detach the cap member 55 from the applicator main body 50, the applying part 57 on which the hair color is adhered comes out, and the applying part 57 is applied onto a hair region to be dyed, whereby the hair can be dyed.

The above applicator C for hair can be an applicator for hair which can suitably be applied to parts such as borders of hair and eyebrows and which is excellent in carrying and handling properties as well as usability, water resistance and a cumulative hair dying property.

EXAMPLES

Next, the present invention shall be explained in further details with reference to examples and comparative examples, but the present invention shall not be restricted by the following examples.

Examples 1 to 5 and Comparative Examples 1 to 4

Components in formulations shown in the following Table 1 were homogeneously stirred and mixed by means of a general purpose propeller mixer to prepare the respective hair colors. MAIBLOCKWAKO 101 (25% ethanol solution, manufactured by Wako Pure Chemical Industries, Ltd., the same shall apply in Table 2) was used for an alkyl acrylate/dimethicone copolymer, and Carbon Black SB-4 manufactured by Degussa Co., Ltd. was used.

The respective hair colors obtained in Examples 1 to 5 and Comparative Examples 1 to 4 described above were measured for a pH and a viscosity by the following methods.

The results thereof are shown in the following Table 1.

Measuring Method of pH

The pH (25° C.) was measured according to a conventional method by means of a glass electrode pH meter.

Evaluating Method of Viscosity

The respective viscosities at 25° C. were measured by means of an ELD type viscometer (manufactured by Toki Sangyo Co., Ltd.)

Then, an applicator for hair having the following constitution shown in FIG. 1 to FIG. 3 was filled with 10 ml of the respective hair colors obtained above to evaluate a cumulative hair dying property, water resistance, a skin dying property and a temporary coloring property by the following methods.

The results thereof are shown in the following Table 1.

Constitution of Applicator for Hair

Feeds: made of PET, intervals of length and breadth between feeds: 3.4 mm, porosity: 80%

Comb parts: made of PBT

Evaluating Method of Cumulative Hair Dying Property

After applied a hair color on 1 g of a hair bundle and dried, twice hair washing was repeated five times, and then the cumulative hair dying property was evaluated according to the following evaluation criteria.

Evaluation criteria

◎: same as commercially available oxidative hair colors

○: no problems on practical use

Δ: a little difficult to be dyed

×: not dyed

Evaluating Method of Water Resistance

After the hair color of about 0.1 ml was applied on 2 g of the hair and dried at room temperature for 120 minutes (hereinafter referred to merely as "after applied on the hairs and dried"), filter paper wetted with water was pressed thereon to evaluate the degree of the color transferred onto the filter paper according to the following evaluation criteria.

Evaluation Criteria

◎: not transferred at all onto filter paper

○: slightly transferred onto filter paper

Δ: a little densely transferred onto filter paper

×: densely transferred onto filter paper

Evaluating Method of Skin Dying Property

The liquid 0.005 g was dropped on an upper arm inside part of a volunteer and left standing for 30 seconds, and then it was wiped away with tissue paper. Thereafter, it was naturally dried, washed with commercial solid soap after one hour and dried. Dying onto the skin was evaluated according to the following evaluation criteria.

Evaluation Criteria

◎: scarcely dyed

○: slightly dyed but not conspicuous

Δ: found to be dyed

×: observed to be obviously dyed

Evaluating Method of Temporary Coloring Property

The liquid 0.1 g was applied on 1 g of a human hair bundle streaked by 10% with gray hairs to evaluate whether or not the gray hairs were masked according to the following evaluation criteria.

Evaluation Criteria

◎: gray hairs could scarcely be distinguished

○: gray hairs were recognized but not conspicuous (shade dying level)

Δ: a little colored but the presence of the gray hairs is observed obviously

×: scarcely colored

TABLE 1

(blend unit: % by weight, whole total amount 100% by weight)

|  | Example 1 | Example 2 | Example 3 | Example 4 | Example 5 | Comparative Example 1 | Comparative Example 2 | Comparative Example 3 | Comparative Example 4 |
|---|---|---|---|---|---|---|---|---|---|
| Refined water | 35 | 35 | 35 | 35 | 40 | 35 | 32 | 35 | 45 |
| Basic dye: | | | | | | | | | |
| BASIC BLUE 99 | 0.3 | 0.3 | 0.3 | 1.2 | 1.8 | 0.3 | — | 0.3 | 3 |
| BASIC RED 76 | 0.2 | 0.2 | 0.2 | 0.8 | 1.2 | 0.2 | — | 0.2 | 2 |
| BASIC YELLOW 57 | 0.2 | 0.2 | 0.2 | 0.8 | 1.2 | 0.2 | — | 0.2 | 2 |
| BASIC BROWN 16 | 0.3 | 0.3 | 0.3 | 1.2 | 1.8 | 0.3 | — | 0.3 | 3 |
| Acidic dye: | | | | | | | | | |
| Black color 401 | | | | | | | 0.04 | | |
| Orange color 205 | | | | | | | 0.5 | | |
| Purple color 401 | | | | | | | 0.2 | | |
| Yellow color 403 (1) | | | | | | | 0.16 | | |
| Ethyl alcohol | 54 | 56 | 45 | 51 | 44 | 57 | 56.1 | 39 | 35 |
| Benzyl alcohol | 5 | 5 | 5 | 5 | 5 | 5 | 5 | 5 | 5 |
| Glycolic acid | | | | | | | 3 | | |
| Alcohol-soluble acryl base resin: (alkyl acrylate/dimethicone) copolymer | 3 | 1 | 12 | 3 | 3 | — | 3 | 18 | 3 |
| Triethanolamine | 2 | 2 | 2 | 2 | 2 | 2 | — | 2 | 2 |
| pH | 7.9 | 7.9 | 8.3 | 8.2 | 8.4 | 7.9 | 3.5 | 8.0 | 8.4 |
| Viscosity (25° C., mPa · s) | 4 | 3.4 | 9.5 | 4.2 | 4.1 | 2.5 | 5 | 35 | 4.5 |
| Five times accumulative dying property | ○ | ○ | ○ | ◎ | ◎ | X | ○ | X | ◎ |
| Water resistance | ◎ | ○ | ◎ | ○ | ○ | X | ○ | ◎ | X |
| Skin dying property | ◎ | ◎ | ◎ | ○ | ○ | ○ | X | ◎ | X |
| Temporary coloring property | ○ | ○ | ○ | ○ | ○ | ○ | ○ | ○ | ○ |

As apparent from the results summarized in Table 1 shown above, it has been found that the hair colors prepared in Examples 1 to 5 falling in the scope of the present invention do not dye the skin and are excellent in all aspects of a cumulative hair dying property, water resistance and a temporary coloring property as compared with those prepared in Comparative Examples 1 to 4 falling outside the scope of the present invention.

To individually observe the comparative examples, Comparative Example 1 is a case where the alcohol-soluble acryl base resin is not added, and it has become clear that the cumulative hair dying property and the water resistance are markedly inferior in this case. Comparative Example 2 is a case where a conventional acid dye is used, and it has become clear that the skin is dyed to bring about a problem in terms of use in this case. Comparative Example 3 is a case where a content of the alcohol-soluble acryl base resin is increased in excess, and it has been found that the cumulative hair dying property is inhibited in this case. Comparative Example 4 is a case where an amount of the basic dye contained is increased in excess, and it has become clear that the water resistance and the skin dying property are markedly inferior in this case.

Example 6 and Comparative Examples 5 to 6

Containing Carbon Black

Components in formulations shown in the following Table 2 were homogeneously stirred and mixed by means of a general purpose turbine mixer to prepare the respective hair colors.

The respective hair colors obtained in Example 6 and Comparative Examples 5 to 6 described above were measured for a pH, a viscosity, a cumulative hair dying property, water resistance, a skin dying property and a temporary coloring property by the methods described above, and dispersibility of carbon black was evaluated by the following method. The results thereof are shown in the following Table 2.

Evaluation Method of Dispersibility of Carbon Black

The hair color was left standing in a sample bottle of 100 ml under 25° C. 65% RH for one day, and then the absence of precipitation of aggregates at a bottle bottom was visually evaluated according to the following evaluation criteria.

Evaluation Criteria

◎: precipitates are not present at a bottle bottom, and a wall surface of the bottle is wetted clearly ○: a trace amount of precipitates is observed at a bottle bottom, but they are homogeneously dispersed by lightly shaking the bottle, and a wall surface of the bottle is wetted clearly Δ: obvious precipitates are observed at a bottle bottom, but they are homogeneously dispersed by strongly shaking the bottle ×: obvious precipitates are observed at a bottle bottom and are not homogeneously dispersed even by a little strongly shaking the bottle

TABLE 2

(blend unit: % by weight, whole total amount 100% by weight)

|  | Example 6 | Comparative Example 5 | Comparative Example 6 |
|---|---|---|---|
| Refined water | 30 | 35 | 30 |
| Basic dye: | | | |
| BASIC BLUE 99 | 0.3 | 0.2 | — |
| BASIC RED 76 | 0.2 | 0.2 | — |

TABLE 2-continued (blend unit: % by weight, whole total amount 100% by weight)

|  | Example | Comparative Example | |
|---|---|---|---|
|  | 6 | 5 | 6 |
| BASIC YELLOW 57 | 0.2 | 0.2 | — |
| BASIC BROWN 16 | 0.3 | 0.3 | — |
| Acidic dye: | | | |
| Black color 401 | | | 0.04 |
| Orange color 205 | | | 0.5 |
| Purple color 401 | | | 0.2 |
| Yellow color 403 (1) | | | 0.16 |
| Carbon black SB-4 | 1.5 | 1.5 | — |
| Ethyl alcohol | 55.5 | 55.5 | 56.1 |
| Benzyl alcohol | 5 | 5 | 5 |
| Glycolic acid | | | 3 |
| Alcohol-soluble acryl base resin: (alkyl acrylate/ dimethicone) copolymer | 5 | — | 5 |
| Triethanolamine | 2 | 2 | — |
| pH | 7.5 | 7.9 | 3.5 |
| Viscosity (25° C., mPa·s) | 4 | 2.5 | 5 |
| Five times accumulative dying property | ○ | X | Δ |
| Water resistance | ◎ | X | ○ |
| Skin dying property | ◎ | ○ | X |
| Temporary coloring property | ◎ | can not be evaluated | Δ |
| Carbon black dispersibility | ◎ | X | ○ |

As apparent from the results summarized in Table 2 shown above, it has been found that the hair color prepared in Example 6 falling in the scope of the present invention does not cause aggregation of carbon black and does not dye the skin as compared with those prepared in Comparative Examples 5 to 6 falling outside the scope of the present invention and that it is excellent in all aspects of a cumulative hair dying property, water resistance and a temporary coloring property.

In contrast with this, to individually observe the comparative examples, Comparative Example 5 is a case where the alcohol-soluble acryl base resin is not added, and it has become clear that the cumulative hair dying property, the water resistance and the carbon black dispersibility are markedly inferior in this case. Comparative Example 6 is a case where a conventional acid dye is used, and it has become clear that the skin is dyed to bring about a problem in terms of use in this case and that the cumulative hair dying property is inferior since the pH is not controlled.

Further, it has been found that a temporary coloring property is further improved in Example 6 by adding carbon black as compared with Examples 1 to 5 in which carbon black is not added.

INDUSTRIAL APPLICABILITY

In the present invention, obtained is a hair color which does not dye the skin and is excellent in a cumulative dying property and which has excellent water resistance against sweat and rain in a hot and humid period such as a summer season, and a user can use with ease by using an applicator for hair filled with the above hair color.

The invention claimed is:

1. A hair color comprising 0.5 to 8% by weight of a basic dye as a coloring agent, 0.5 to 15% by weight of an alcohol-soluble acryl base resin, 20 to 80% by weight of a lower alcohol and 5 to 50% by weight of water.

2. The hair color as described in claim 1, wherein the alcohol-soluble acryl base resin is a silicone acryl block copolymer.

3. A hair color comprising 0.5 to 15% by weight of a basic dye as a coloring agent, 0.5 to 15% by weight of an alcohol-soluble acryl base resin, 20 to 80% by weight of a lower alcohol, 5 to 50% by weight of water, and carbon black.

4. A hair color comprising 0.5 to 8% by weight of a basic dye as a coloring agent, 0.5 to 15% by weight of an alcohol-soluble acryl base resin, 20 to 80% by weight of a lower alcohol, 5 to 50% by weight of water, and carbon black, wherein the alcohol-soluble acryl base resin is a silicone acryl block copolymer.

5. The hair color as described in claim 3, wherein a content of the carbon black is 0.1 to 3% by weight based on the total amount of the hair color.

6. The hair color as described in claim 4, wherein a content of the carbon black is 0.1 to 3% by weight based on the total amount of the hair color.

7. A hair color comprising 0.5 to 8% by weight of a basic dye as a coloring agent, 0.5 to 15% by weight of an alcohol-soluble acryl base resin, 20 to 80% by weight of a lower alcohol and 5 to 50% by weight of water, wherein the hair color has a viscosity of 20 mPa·s or less.

8. A hair color comprising 0.5 to 8% by weight of a basic dye as a coloring agent, 0.5 to 15% by weight of a silicone acryl block copolymer, 20 to 80% by weight of a lower alcohol and 5 to 50% by weight of water, wherein the alcohol-soluble acryl base resin is a silicone acryl block copolymer, and the hair color has a viscosity of 20 mPa·s or less.

9. The hair color as described in claim 3, wherein the hair color has a viscosity of 20 mPa·s or less.

10. The hair color as described in claim 4, wherein the hair color has a viscosity of 20 mPa·s or less.

11. The hair color as described in claim 5, wherein the hair color has a viscosity of 20 mPa·s or less.

12. The hair color as described in claim 6, wherein the hair color has a viscosity of 20 mPa·s or less.

* * * * *